United States Patent

Ogura et al.

[11] Patent Number: 5,243,984
[45] Date of Patent: Sep. 14, 1993

[54] METHOD AND APPARATUS FOR DETERMINING BIOCURRENT DISTRIBUTION WITHIN SUBJECT

[75] Inventors: Yukiko Ogura, Kokubunji; Kensuke Sekihara, Musashimurayama; Hisaaki Ochi, Kunitachi, all of Japan

[73] Assignee: Hitachi, Ltd., Tokyo, Japan

[21] Appl. No.: 928,782

[22] Filed: Aug. 13, 1992

[30] Foreign Application Priority Data

Aug. 13, 1991 [JP] Japan .................. 3-202720

[51] Int. Cl.⁵ .............................................. A61B 5/05
[52] U.S. Cl. ................................ 128/653.1; 128/731; 128/734; 364/413.02
[58] Field of Search ............... 128/653.1, 653.2, 731, 128/732, 734; 364/413.01, 413.02

[56] References Cited

U.S. PATENT DOCUMENTS 4,736,751 4/1988 Gevins et al. ............... 128/732
4,770,182 9/1988 Damadian et al. ........... 128/653.2
5,170,119 12/1992 Sekihara et al. ............. 128/653.1

FOREIGN PATENT DOCUMENTS 355506 2/1990 European Pat. Off. ............. 128/731
449231 10/1991 European Pat. Off. ............. 128/731

OTHER PUBLICATIONS

Electro Medica, vol. 57, No. 1, 1989, Erlangen (DE), pp. 2–7, XP8302 F. Gudden et al. "Ein vielkanalsystem zur biomagnetischen diagnostik in neurologie and kardiologie: prinzip, methode und erste ergebnisse".
SPIE, vol. 1351, Digital Image Synthesis and Inverse Optics (1990); pp. 410–416.
Colophon of Numerical Calculation of Matrix.

Primary Examiner—Kyle L. Howell
Assistant Examiner—George Manuel
Attorney, Agent, or Firm—Antonelli, Terry, Stout & Kraus

[57] ABSTRACT

A living body is replaced by a 3-D network. Admittance connected to lines forming the 3-D network is calculated. Position rt and magnitude $qt = (jtx, jty, jtz)$ of a current dipole are assumed, and current sources $jtx$, $jty$ and $jtz$ are connected in parallel with lines coupled to a node. Node equations are formulated, and an admittance matrix Y is derived. An inverse matrix Y' of Y is calculated, and body surface potential generated by the current sources is calculated by using the inverse matrix Y'. Then, rt and qt minimizing cost function which is sum total of squares of differences between measured values of body surface potential and the above described calculated values for all measuring points are derived. Thereby potential distribution on the body surface can be calculated with due regard to the shape of the living body and conductivity distribution in the living body on the basis of the assumed current dipole. On the basis of measured data of potential distribution on the body surface, therefore, the position and magnitude of the current dipole can be estimated with high precision.

22 Claims, 13 Drawing Sheets

F I G. 5
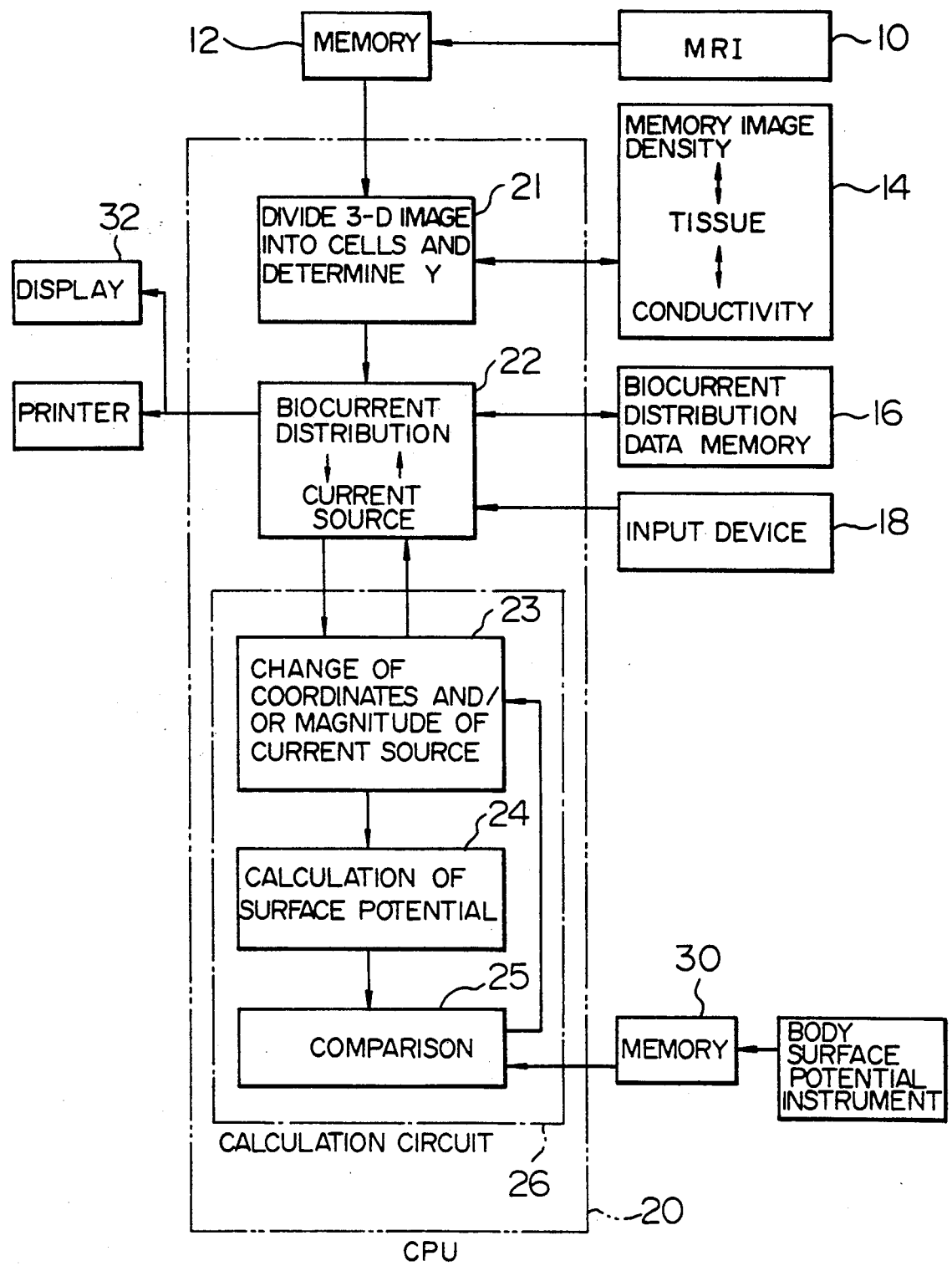

FIG. 7
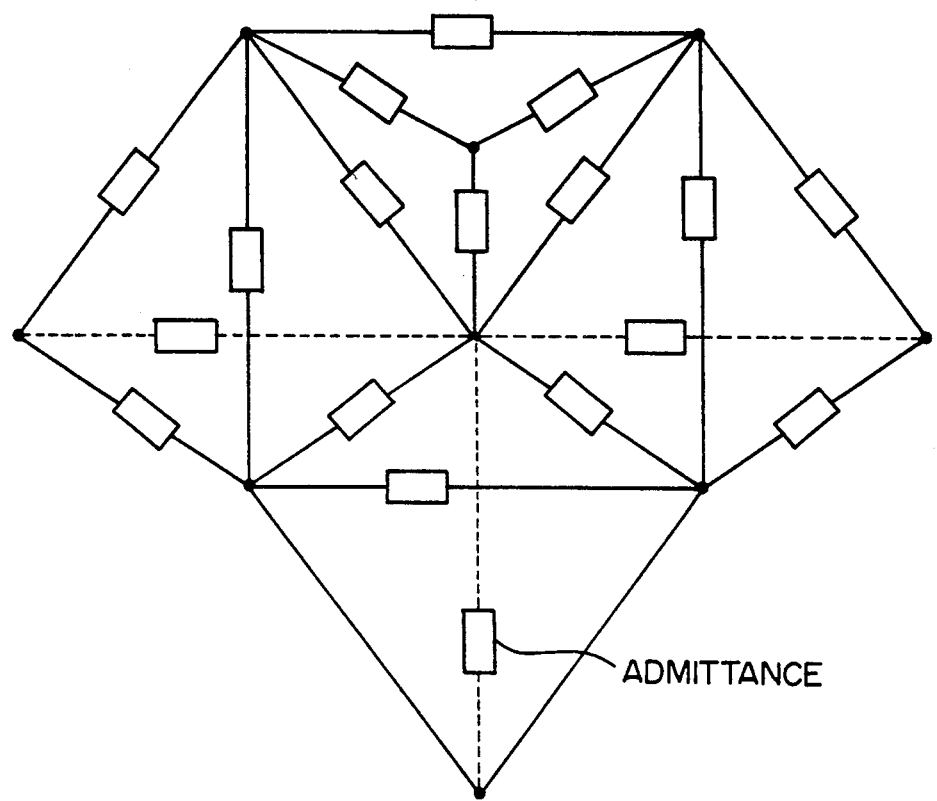
ADMITTANCE
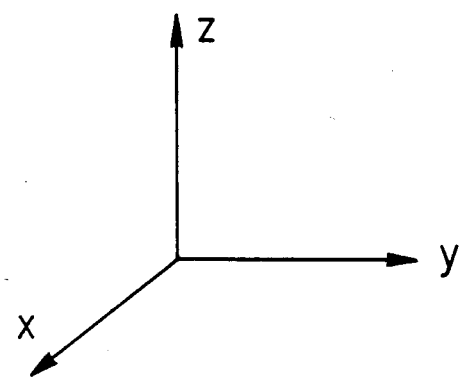

METHOD AND APPARATUS FOR DETERMINING BIOCURRENT DISTRIBUTION WITHIN SUBJECT

BACKGROUND OF THE INVENTION

The present invention relates to a method, and apparatus, for determining biocurrent distribution within a subject, and in particular to a technique for indirectly deriving a biocurrent distribution, particularly a biocurrent distribution in a brain.

Determination of such a biocurrent distribution is applied to some diagnoses as described in "Biomagnetic multichannel measurements in the pre-operative diagnostic evaluation of epilepsy," Electromedica 4/1989, which is incorporated herein by reference.

As for methods for estimating biocurrent distribution on the basis of distribution of living body surface potential derived by measurement, several methods have already been proposed as the method of representing biocurrent distribution by using a current dipole model and of calculating distribution of living body surface potential on the basis of the assumed current dipole.

Salu et al. assumed that the head had three concentric spheres having different conductivities and analytically calculated potentials generated on the head surface by current dipoles (IEEE Transactions on Biomedical Engineering, vol. 7, pp. 699-705, 1990).

Aoki et al. calculated the distribution of living body surface potential by using the boundary element method (Journal of Medical Electronics and Biological Engineering, 22-5, pp. 318-323, 1984). Further, Yamanishi et al. calculated the distribution of living body surface potential by using the finite element method (Journal of Medical Electronics and Biological Engineering, 18-2, pp. 126-132, 1980). These methods are effective as the approach for calculating the distribution of body surface potential in case where the distribution of conductivity in a subject body is not uniform and has an asymmetric shape. However, these methods need a lot of time.

SUMMARY OF THE INVENTION

An object of the present invention is to provide a novel method for determining biocurrent distribution on the basis of distribution of living body surface potential. This method makes it possible to derive biocurrent distribution accurately in a short time.

When biocurrent distribution is to be estimated from potential distribution on the surface of a body to be measured, it is assumed that a current dipole having an arbitrary position and an arbitrary magnitude is present in the living body. Then potential distribution generated on the body surface at that time is calculated, and the position and magnitude of a current dipole which generates the body surface potential distribution coinciding with the above described potential distribution on the surface of the body to be measured. When the potential distribution on the body surface is to be calculated from the assumed current dipole, it is necessary to consider a human body model with the shape of the human body and conductivity distribution within the human body taken into account.

When biocurrent distribution within a living body is to be estimated from measured potential distribution on the body surface, it is necessary to derive potential distribution on the body surface generated from arbitrary biocurrent distribution assumed in the living body.

In accordance with the present invention, biocurrent distribution within a living body is represented by at least one current source and the inside of the living body is represented as a network so that potential distribution on the human body surface generated by a current dipole having a arbitrary shape and arbitrary conductivity distribution and positioned within the living body may be calculated. That is to say, the living body is divided into fine cells, and then admittances calculated from physical properties such as conductivities of respective cells are connected to replace a subject by a 3-D network and numerically solve for node voltage of the 3-D network. Individual cells can be provided with anisotropy in each direction, and conductivities are anatomically derived. As for the head, for example, conductivities of tissues forming brain organs, skull and scalp are already known from the anatomical point of view. Therefore, a tissue within a living body is discriminated by using MRI or X-ray CT, and the conductivity of a cell corresponding to that tissue is determined. When the cell extends over two or more tissues, the conductivity of that cell is determined by considering proportions of respective tissues in that cell. To be concrete, proportions of respective tissues are multiplied by their conductivities and the sum total of resultant products is derived.

First of all, the inside of a living body is divided into (I,J,K) cells. Admittances Yx(i,j,k), Yy(i,j,k) and Yz(i,j,k) calculated by the following equations are connected to each line of each cubic cell as shown in FIGS. 1 and 2.

$$Yx(i, j, k) = \frac{s(i, j, k)cb}{a} \quad (1)$$

$$Yy(i, j, k) = \frac{s(i, j, k)ac}{b} \quad (2)$$

$$Yz(i, j, k) = \frac{s(i, j, k)ba}{c} \quad (3)$$

In these equations, $s(i,j,k)$ is conductivity of a $(i,j,k)$-th cell. Further, a, b and c represent side lengths of the cell in x, y and z directions, respectively. Biocurrent distribution in the living body can be represented in terms of coordinates and magnitudes of current dipoles. Further, a current dipole can be represented as a current source in a 3-D network. Now, let the magnitude of a t-th current dipole included in T current dipoles be Jtx, Jty and Jtz respectively in x, y and z directions, and let the node where the t-th current dipole is positioned be (it,jt,kt). Then, in the 3-D network, current sources respectively having current magnitudes Jtx, Jty and Jtz are connected between a node (it,jt,kt) and a node (it+1,jt,kt), between a node (it,jt,kt) and a node (it,jt+1,kt), and between a node (it,jt,kt) and a node (it,jt,kt+1), respectively. Letting at this time the potential at the node (i,j,k) of the cell be V(i,j,k) and the sum of currents flowing into the node (i,j,k) be J(x,y,z), the following equation is obtained from the Kirchhoff's first law prescribing that the sum total of currents flowing into an arbitrary node is zero.

$$\begin{aligned}
&V(i, j, k)(Yx(i, j, k) + Yy(i, j, k) + Yz(i, j, k) + \\
&\quad Yx(i-1, j, k) + Yy(i, j-1, k) + Yz(i, j, k-1)) - \\
&\quad V(i+1, j, k)Yx(i, j, k) - V(i, j+1, k)Yy(i, j, k) - \\
&\quad V(i, j, k+1)Yz(i, j, k) - V(i-1, j, k)Yx(i-1, j, k) - \\
&\quad V(i, j-1, k)Yy(i, j-1, k) - V(i, j, k-1)Yz(i, j, k-1) = \\
&\quad J(i, j, k)
\end{aligned} \quad (4)$$

Replacing V(i,j,k) and J(x,y,z) as $$E1 = V(1, 1, 1)$$
$$E2 = V(2, 1, 1) \quad (5)$$
$$E3 = V(3, 1, 1)$$
$$\vdots$$
$$En = V(I, J, K)$$

and $$J1 = J(1, 1, 1)$$
$$J2 = J(2, 1, 1) \quad (6)$$
$$J3 = J(3, 1, 1)$$
$$\vdots$$
$$Jn = J(I, J, K),$$

equation (4) can be expressed as $$\begin{bmatrix} y11 & y12 & \cdots & y1n-1 \\ y21 & y22 & \cdots & y2n-1 \\ \vdots & \vdots & & \vdots \\ yn-11 & yn-12 & \cdots & yn-1n-1 \end{bmatrix} \begin{bmatrix} E1 \\ E2 \\ \vdots \\ En-1 \end{bmatrix} = \begin{bmatrix} J1 \\ J2 \\ \vdots \\ Jn-1 \end{bmatrix}$$

where $$ypp = Yx(i, j, k) + Yy(i, j, k) + Yz(i, j, k) + Yx(i-1, j, k) + Yy(i, j-1, k) + Yz(i, j, k-1)$$

$$ypq = -Yx(i-1, j, k) \quad (7)$$
$$ypr = -Yy(i, j-1, k)$$
$$yps = -Yz(i, j, k-1).$$

Therefore, the position and/or current magnitude of a current source representing a current dipole is arbitrarily changed, and the potential at each node is derived by the following equation.

$$\begin{bmatrix} E1 \\ E2 \\ \vdots \\ En-1 \end{bmatrix} = Y \begin{bmatrix} J1 \\ J2 \\ \vdots \\ Jn-1 \end{bmatrix} \quad (8)$$

Cost function C is defined by the following equation.

$$C = \sum_{m=1}^{M} |Fm - Gm|^2 \quad (9)$$

By deriving Jtx, Jty, Jtz and (it,jt,kt) minimizing C, estimation of the position and magnitude of the current dipole is accomplished. In this equation, Fm denotes measured potential distribution on the body surface, whereas Gm denotes potential distribution on the body surface calculated from the assumed current source.

From the position and magnitude of the current dipole, biocurrent distribution within the subject is derived.

Those skilled in the art can easily expect that the combination of the above described current source and admittance can be replaced by a combination of a voltage source and impedance. Use of the latter combination will now be described in detail.

We now consider a 3-D network as a human body model as shown in FIG. 1. It is assumed that T current dipoles indicating biocurrent distribution within a living body can be expressed by 3T current sources. If it is assumed that the position and magnitude of a t-th current dipole are respectively (it,jt,kt) and (Jtx,Jty,Jtz), a current source representing a current dipole in the 3-D network which is a human body model is considered to be a current source having a voltage source ex(i,j,k) serially connected to impedance Zx(in,jn,kn), a voltage source ey(i,j,k) serially connected to impedance Zy(in,jn,kn), and a voltage source ez(i,j,k) serially connected to impedance Zz(in,jn,kn). Ix(i,j,k), Iy(i,j,k) and Iz(i,j,k) are loop currents flowing through loops respectively perpendicular to x, y and z axes including the node (i,j,k). Zx(i,j,k), Zy(i,j,k) and Zz(i,j,k) are impedances positioned in lines which are respectively parallel to x axis, y-axis and z-axis directions, and are expressed as $$Zx = \frac{a}{s(i, j, k)bc} \quad (10)$$

$$Zy = \frac{b}{s(i, j, k)ca} \quad (11)$$

$$Zz = \frac{c}{s(i, j, k)ab} \quad (12)$$

where a, b and c are side lengths of the cell in the x, y and z directions, respectively. Impedance values expressed by equations (10), (11) and (12) are derived by a method hereafter described. In the same way as the case of admittance, a three-dimensional magnetic resonance image or x-ray image is divided into IJK cells, and impedance values are derived from equations (10), (11) and (12) by using conductivities of a living body tissue in respective cells. From the Kirchhoff's second law, we get $$Ix(i, j, k) [Zy(i, j, k) + Zy(i, j, k+1) + Zz(i, j, k) + Zz(i, j+1, k)] + [Iz(i-1, j, k) - Iz(i, j, k) - Ix(i, j, k-1)]Zy(i, j, k) + [Iz(i, j, k+1) - Iz(i-1, j, k+1) - Ix(i, j, k+1)]Zy(i, j, k+1) + [Iy(i-1, j, k) - Iy(i, j, k) - Ix(i, j-1, k)]Zz(i, j, k) + [Iy(i, j+1, k) - Iy(i-1, j+1, k) - Ix(i, j+1, k)]Zz(i, j+1, k) = Ex(i, j, k)$$

where $$Ex(x,j,k) = ey(i,j,k) + ez(i,j,k) \quad (13\text{-}1)$$

$$Iy(i, j, k) [Zx(i, j, k) + Zx(i, j, k+1) + Zz(i, j, k) + Zz(i+1, j, k)] + [Ix(i-1, j, k) - Ix(i, j, k) - Iy(i-1, j, k)]Zx(i, j, k) + [Ix(i+1, j, k) - Iy(i-1, j, k)]Zx(i, j, k) + [Ix(i+1, j-1, k) - Iy(i+1, j, k)]Zz(i+1, j, k) + [Iz(i-1, j, k) - Iz(i, j, k) - Iy(i, j, k-1)]Zx(i, j, k) +$$

-continued
$$[Iz(i, j, k + 1) - Iz(i, j - 1, k + 1) - Iy(i, j, k + 1)]Zx(i, j, k + 1) = Ey(i, j, k)$$

where $$Ey(i,j,k) = ez(i,j,k) + ex(i,j,k) \quad (13\text{-}2)$$

and $$Iz(i, j, k) [Zx(i, j, k) + Zx(i, j + 1, k) + Zy(i, j, k) + Zy(i + 1, j, k)] + [Iy(i, j, k - 1) - Iy(i, j, k) - Iz(i, j - 1, k)]Zx(i, j, k) + [Iy(i, j + 1, k) - Iy(i, j + 1, k - 1) - Iz(i, j, k + 1)]Zx(i, j + 1, k) + [Ix(i, j, k - 1) - Ix(i, j, k) - Iz(i - 1, j, k)]Zy(i, j, k) + [Ix(i + 1, j, k) - Ix(i + 1, j, k - 1) - Iz(i + 1, j, k)]Zy(i + 1, j, k) = Ez(i, j, k)$$

where $$Ez(i,j,k) = ex(i,j,k) + ey(i,j,k). \quad (13\text{-}3)$$

Ex(i,j,k) denotes the sum of voltage sources connected to the loop which is perpendicular to the x-axis and which includes the node (i,j,k). These equations are formed for all loops, and solutions Ix(i,j,k), Iy(i,j,k) and Iz(i,j,k) satisfying L-IJK+1 simultaneous equations are derived, where L is the number of lines. Ix(i,j,k), Iy(i,j,k) and Iz(i,j,k) are derived by using a method hereafter described. First of all, Ix(i,j,k), Iy(i,j,k), Iz(i,j,k), Ex(i,j,k), Ey(i,j,k) and Ez(i,j,k) are replaced as indicated by the following equations.

$$\begin{aligned} I1 &= Ix(1, 1, 1) \\ I2 &= Iy(1, 1, 1) \\ I3 &= Iz(1, 1, 1) \\ &\cdot \\ &\cdot \\ In &= Iz(I, J, K) \end{aligned} \quad (14)$$

$$\begin{aligned} ES1 &= Ex(1, 1, 1) \\ ES2 &= Ey(1, 1, 1) \\ ES3 &= Ez(1, 1, 1) \\ &\cdot \\ &\cdot \\ ESn &= Ez(I, J, K) \end{aligned} \quad (15)$$

In these equations, n=IJK. At this time, equations (13-1) to (13-3) are rewritten and the following equation is obtained.

$$\begin{bmatrix} z11 & z12 & \ldots & z1n \\ z21 & z22 & \ldots & z2n \\ \cdot & \cdot & & \cdot \\ \cdot & \cdot & & \cdot \\ zn1 & zn2 & \ldots & znn \end{bmatrix} \begin{bmatrix} I1 \\ I2 \\ \cdot \\ \cdot \\ In \end{bmatrix} = \begin{bmatrix} ES1 \\ ES2 \\ \cdot \\ \cdot \\ ESn \end{bmatrix} \quad (16)$$

We define a matrix Z by the following equation.

$$Z = \begin{bmatrix} z11 & z12 & \ldots & z1n \\ z21 & z22 & \ldots & z2n \\ \cdot & \cdot & & \cdot \\ \cdot & \cdot & & \cdot \\ zn1 & zn2 & \ldots & znn \end{bmatrix} \quad (17)$$

The matrix Z can be derived beforehand as the state having no voltage sources at all. Therefore, I1, I2,...,In can be derived by the following equation.

$$\begin{bmatrix} I1 \\ I2 \\ \cdot \\ \cdot \\ In \end{bmatrix} = Z' \begin{bmatrix} ES1 \\ ES2 \\ \cdot \\ \cdot \\ ESn \end{bmatrix} \quad (18)$$

Z' is the inverse matrix of Z. Further, since I1,I2,...,In can be independently calculated, Im can be calculated by using the following equation in a parallel processing computer.

$$Im = [z'm1 \; z'm2 \; \ldots \; z'mn] \begin{bmatrix} Es1 \\ ES2 \\ \cdot \\ \cdot \\ ESn \end{bmatrix} \quad (19)$$

The row vector [Z'm1,Z'm2,...,Z'mn] is an element of the m-th row of a matrix Z' represented by the following equation.

$$Z' = \begin{bmatrix} z'11 & z'12 & \ldots & z'1n \\ z'21 & z'22 & \ldots & z'2n \\ \cdot & \cdot & & \cdot \\ \cdot & \cdot & & \cdot \\ z'n1 & z'n2 & \ldots & z'nn \end{bmatrix} \quad (20)$$

Since the current flowing through each line and the impedance of that line are determined as heretofore described, the potential difference between nodes located at both ends of each line is determined. If one node is selected as the reference potential, therefore, potentials of all nodes are determined. By using the cost function of equation (9), therefore, current distribution is estimated.

BRIEF DESCRIPTION OF THE DRAWINGS

These and other objects and technical advantages of the present invention will be readily apparent from the following description of the preferred exemplary embodiments of the invention in conjunction with the accompanying drawings, in which:

FIG. 5 is a block diagram showing the configuration of an embodiment of a biocurrent distribution determining apparatus according to the present invention;

FIGS. 7 and 8 show variant versions of cell implementation;

DESCRIPTION OF THE PREFERRED EMBODIMENTS

Embodiment 1

Figure 4:
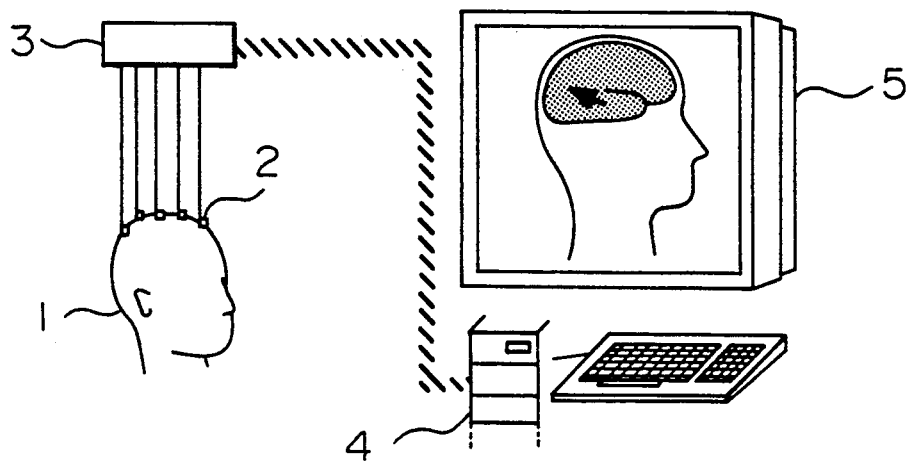
FIG. 4 is a schematic configuration diagram of an embodiment of a living body surface potential distribution measuring apparatus according to the present invention.

FIG. 4 shows an embodiment of a living body surface potential measuring apparatus according to the present invention. A plurality of sensors 2 are attached to the head surface of a subject 1. The sensors 2 measure potentials of the head surface, amplify signals corresponding to the potentials, and transmit the amplified signals to an A/D converter 3. Those signals are converted into digital signals by the A/D converter and supplied to a computer 4. As this potential measuring apparatus, EEG-4421Q (brain waveform) produced by Nippon Koden Ltd. is used.

Figure 6:
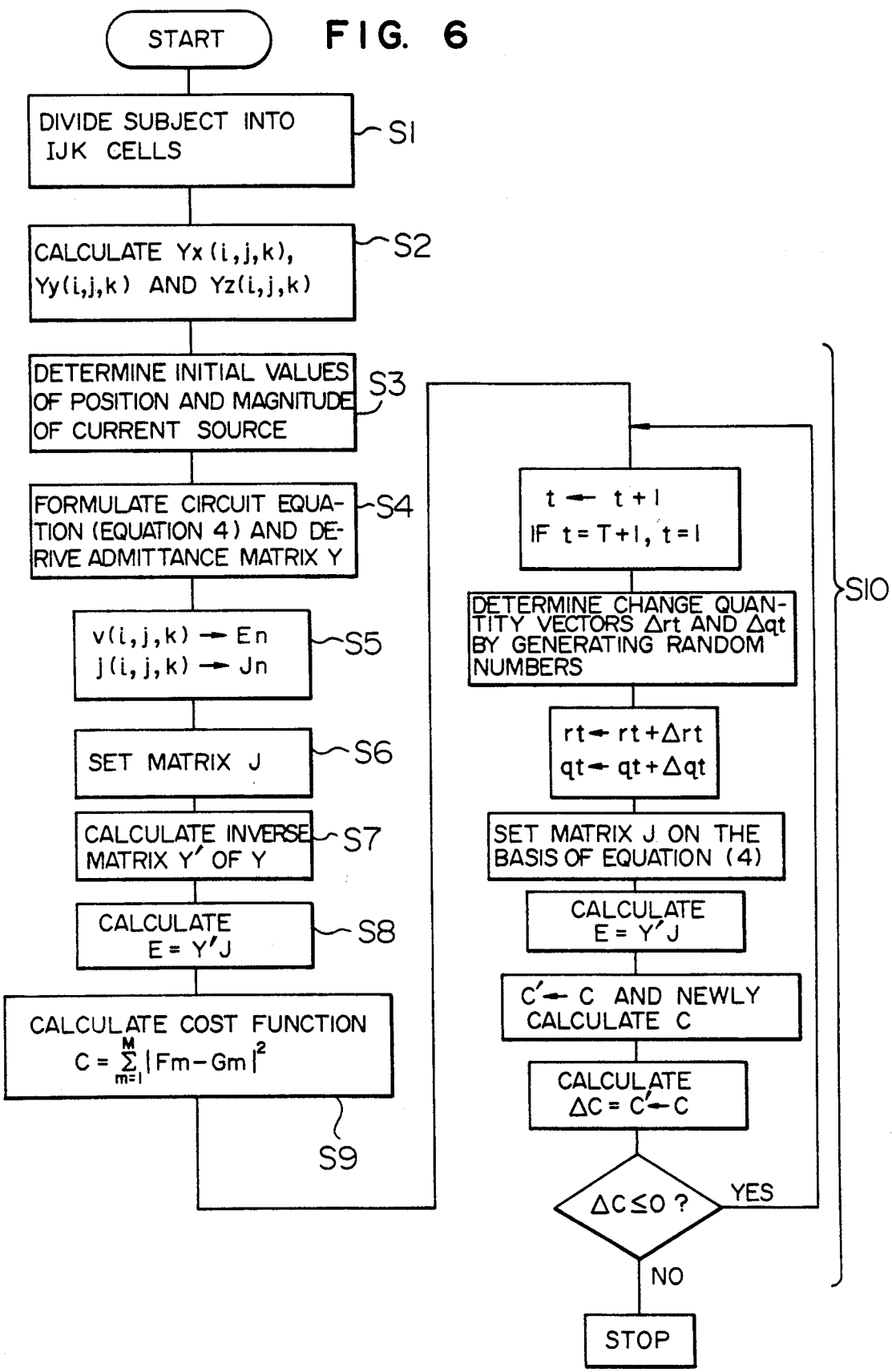
FIG. 6 is a flow chart for explaining the operation of the apparatus of FIG. 5.

FIG. 5 is a schematic configuration diagram of an embodiment of a biocurrent distribution determining apparatus according to the present invention. FIG. 6 is a flow chart showing the method of this embodiment. By further referring to FIGS. 1 and 2, the biocurrent distribution determining method of the present embodiment will hereafter be described.

First of all, a three-dimensional image of the head of a subject is generated by an MRI (Magnetic Resonance Imaging) apparatus 10. As the MRI apparatus, trade name MRH-500 produced by Hitachi Medico (Ltd.) is preferably used. Use of an X-ray CT apparatus instead of an MRI apparatus will readily occur to those skilled in the art. As the X-ray CT apparatus, trade name CT-W2000 produced by Hitachi Medico (Ltd.) can be used. The three-dimensional image of the head thus obtained is preserved in a memory 12 as image data.

Figure 2:
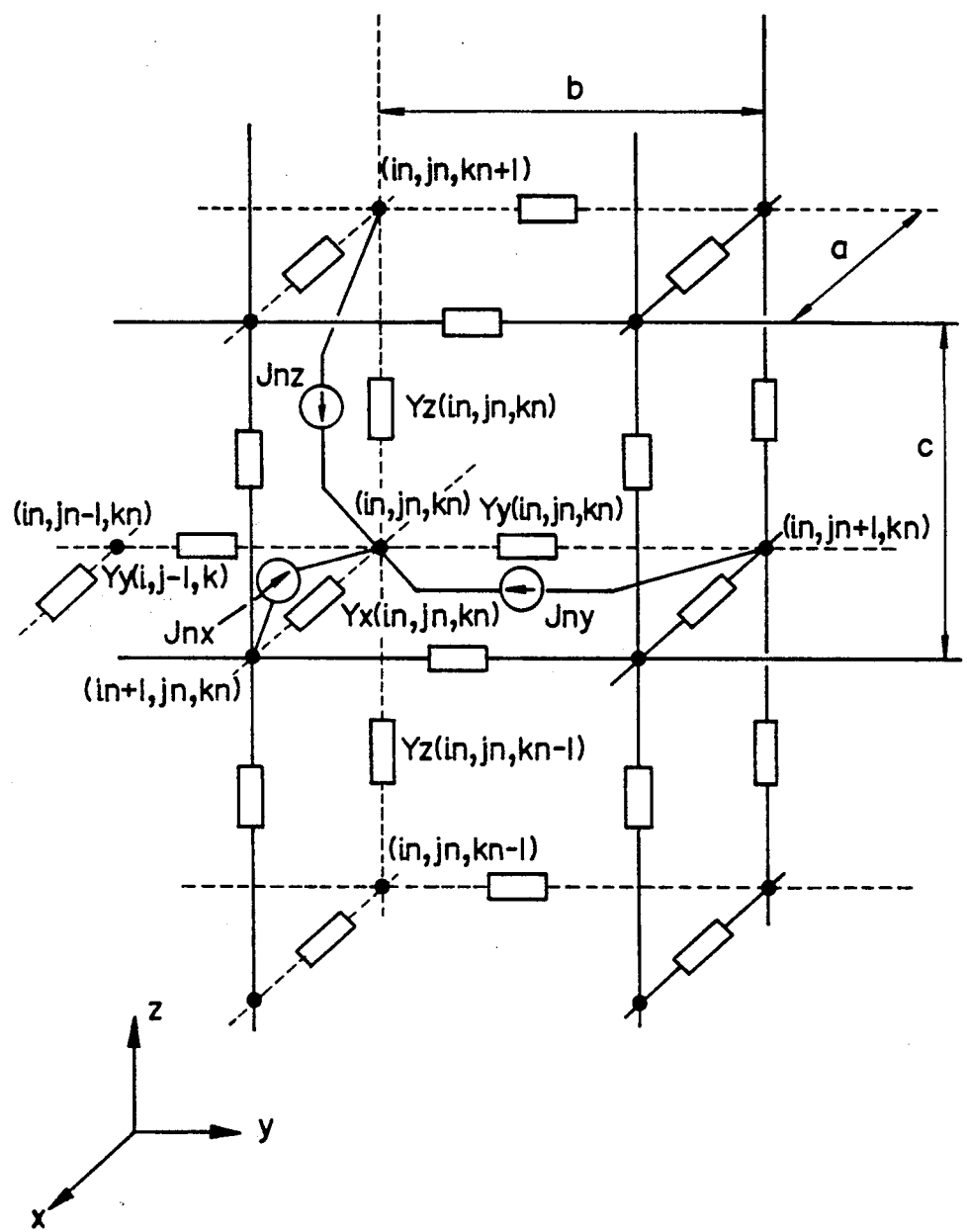
FIG. 2 is an equivalent diagram of a cell shown in FIG. 1 obtained by representing current distribution assumed in the subject by a current source and representing conductivity of the subject by admittance.
Figure 3:
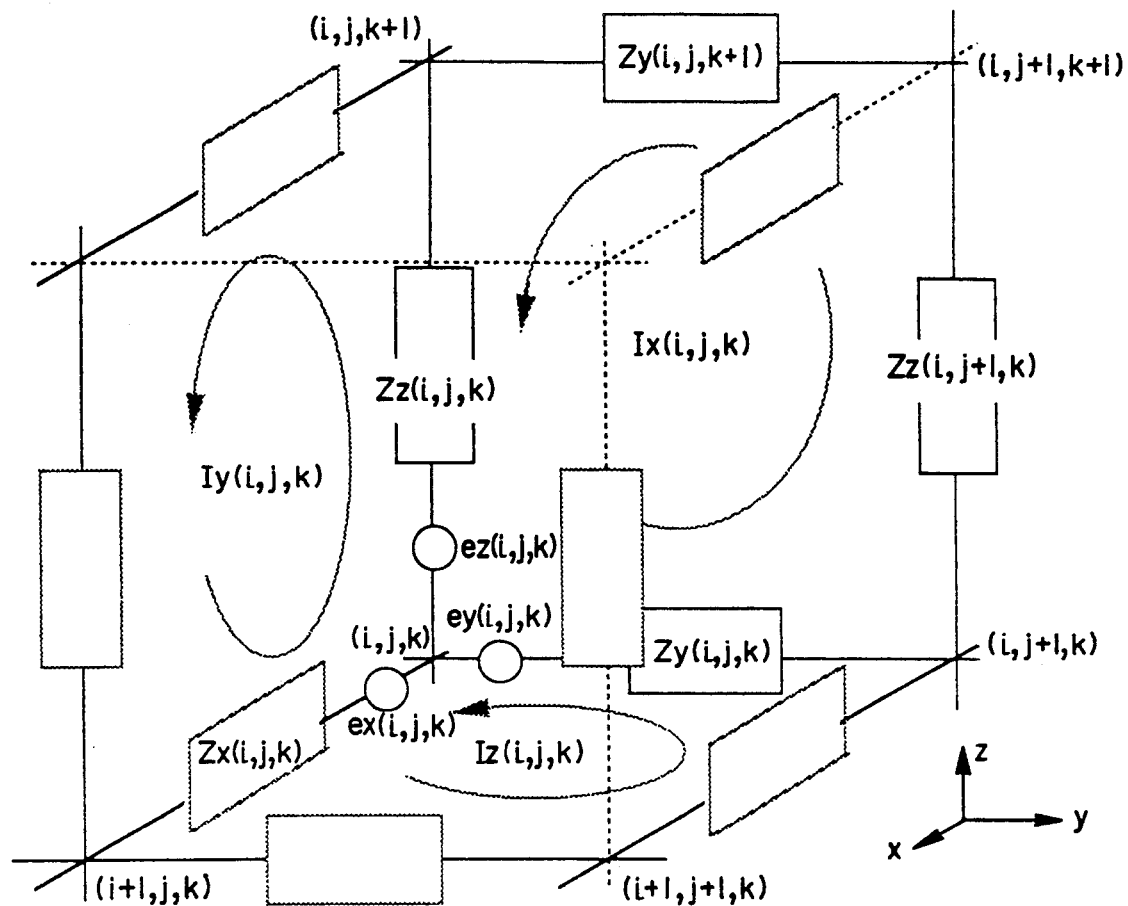
FIG. 3 is an equivalent diagram of the cell shown in FIG. 1 obtained by representing current distribution assumed in the subject by a voltage source and representing conductivity of the subject by impedance.

Then a first circuit 21 reads out that image and divides it into IJK-cells (step 1). By referring to data stored in a memory 14, the first circuit 21 determines admittance of lines defining the exterior shape of a cell as shown in FIG. 2 (step 2). It is assumed that a cell has a size of 1 cm×1 cm×1 cm. In the memory 14, data concerning densities of a three-dimensional image (- strength of signals at respective pixels) derived in the MRI apparatus, relations to tissues forming the head, and relations between tissues and their conductivities are preserved. Thereby the first circuit 21 can determine admittances of lines.

Admittances $Yx(i,j,k)$, $Yy(i,j,k)$ and $Yz(i,j,k)$ are admittances positioned on lines which are parallel to the x-axis, y-axis and z-axis, respectively. These admittances are given by equations (1), (2) and (3) described before. In those equations, a, b and c denote side lengths of the cell in the x, y and z directions, respectively.

By using an input device 18, the operator then specifies assumed current distribution, i.e., coordinates and magnitudes of current dipoles in the same three-dimensional image. This assumption of biocurrent distribution may be uniquely determined according to kinds of diagnosis and preserved in a memory 16 beforehand. Alternatively, biocurrent distribution determined by preceding processing may be preserved in the memory 16 beforehand so as to be used as assumed biocurrent distribution.

Letting the position of the current dipole thus assumed and the current vector be $rt=(it,jt,kt)$ and $qt=(Jtx,Jty,Jtz)$ respectively, a second circuit 22 determines current sources indicating current dipoles in the three-dimensional network formed by lines as shown in FIG. 2 (step 3). A current source Jtx is connected in parallel with admittance $Yx(in,jn,kn)$ and a current source Jty is connected in parallel with admittance $Yy(in,jn,kn)$, whereas a current source Jtz is connected in parallel with admittance $Yz(in,jn,kn)$. $V(i,j,k)$ denotes potential at a node $(i,j,k)$.

On the basis of such current sources, a fourth circuit 24 then calculates potentials at respective nodes by using the method already described (equations 4 to 8, steps 5 to 8).

That is to say, the above described equation (4) holds true on the basis of the Kirchhoff's first law, i.e., node law. $J(i,j,k)$ denotes the sum of current sources flowing into the node $(i,j,k)$. These equations are formulated for all nodes, and solution $V(i,j,k)$ satisfying n simultaneous equations is derived.

$V(i,j,k)$ is derived by using a method hereafter described. First of all, one-dimensional numbers are reassigned to all nodes, and $V(i,j,k)$ and $J(i,j,k)$ are replaced as indicated by equations (5) and (6). However, one equation included in n simultaneous equations is linear dependent. Therefore, one arbitrary equation included in n simultaneous equations can be omitted. If it is assumed that the potential at the n-th node is 0, for example, the equation at the n-th node can be omitted and equation (4) can be rewritten as indicated by equation (7). In equation (7), p, q, r and s denote numbers of nodes $(i,j,k)$, $(i-1,j,k)$, $(i,j-1,k)$ and $(i,j,k-1)$, respectively. That is to say, the product of the admittance matrix and the column matrix E becomes equal to the column matrix J. We here define admittance matrix Y as $$Y = \begin{bmatrix} y11 & y12 & \ldots & y1n-1 \\ y21 & y22 & \ldots & y2n-1 \\ \cdot & \cdot & & \cdot \\ \cdot & \cdot & & \cdot \\ \cdot & \cdot & & \cdot \\ yn-11 & yn-12 & \ldots & yn-1n-1 \end{bmatrix} \quad (21)$$

The matrix Y is derived beforehand assuming that in equation (4) there are no current sources at all, i.e., $J(x,y,z)=0$ for all nodes. Therefore, E1, E2, ..., En can be derived by means of equation (8). Y' is the inverse matrix of Y. Since E1, E2, ..., En can be calculated independently, they can be calculated by using the following equation in a parallel processing computer.

$$Em = [y'm1 \ y'm2 \ ... \ y'mn - 1] \begin{bmatrix} J1 \\ J2 \\ \vdots \\ Jn \end{bmatrix} \quad (22)$$

The row vector [y'm1,y'm2,...,y'mn] is the m-th row element of the matrix Y' represented by the following equation.

$$Y' = \begin{bmatrix} y'11 & y'12 & ... & y'1n-1 \\ y'21 & y'22 & ... & y'2n-1 \\ \vdots & \vdots & & \vdots \\ y'n-11 & y'n-12 & ... & y'n-1n-1 \end{bmatrix} \quad (23)$$

It is not necessary to derive all of the values of E1, E2, .., En, but it is necessary to only calculate at least the potential at the same point as the node where the body surface potential has been measured.

On the other hand, the surface potential of the head is measured by the apparatus of FIG. 4 and preserved in a memory 30 beforehand. Points whereat the surface potential is measured are made to coincide with nodes of the network formed by lines.

At step 9, the cost function expressed by equation (9) is calculated by taking the measured potential value at the m-th measured node as Fm and taking the potential calculated from the above described current sources assumed in the living body at the above described nodes whereat body surface potential has been measured as Gm. M is the number of measuring points. Gm is the potential included in E1, E2, ..., En, which is measured at the same point as the node where the body surface potential has been measured. This calculation is performed by a comparison circuit 25.

At step 10, a third circuit 23 suitably selects positions and magnitudes of T current sources, sets the matrix J, derives E1, E2, ..., En or M Gm's, and selects a matrix J minimizing the cost function. The solution thus selected becomes optimum estimated values of positions and magnitudes of current sources Concrete execution of this step 10 is described in U.S. patent application Ser. No. 07/676077, filed Mar. 27, 1991 and incorporated herein by reference.

Once the optimum positions and magnitudes of current sources are thus determined, the second circuit 22 derives biocurrent distribution and displays it on a display 32. On the display 32, the MRI image and the image indicating the above described resultant biocurrent distribution are superposed.

Figure 1:
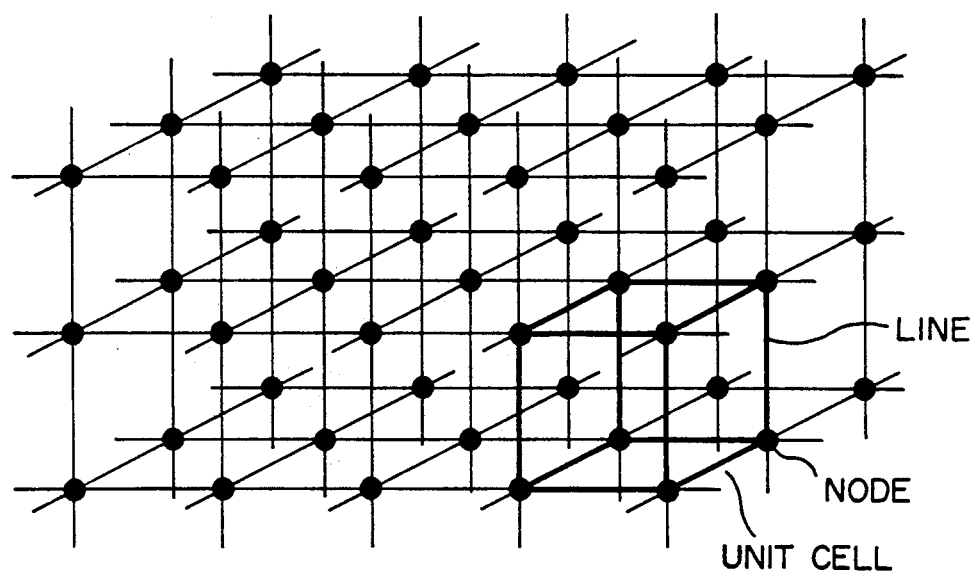
FIG. 1 is an oblique view showing a cell assumed in a subject.

In this embodiment, current distribution has been estimated by replacing a living body by the circuit forming the cubic cell network as shown in FIG. 1. However, the circuit is not limited to this, but other 3-D networks can be used as a living body model. FIG. 7 shows a living body model forming a tetrahedral network in which each side is represented by a triangle.

Figure 8:
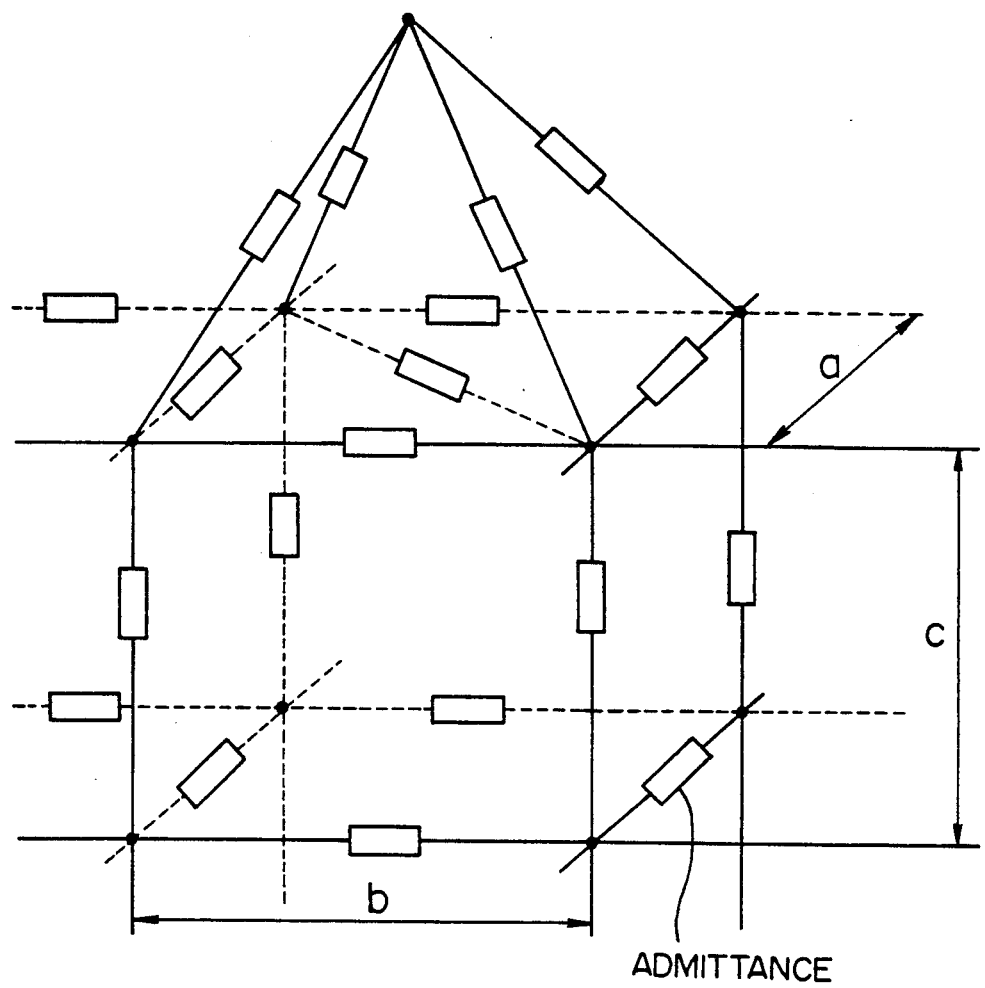

FIG. 8 shows a living body model network in which a part of the cubic cell network is replaced by a triangle according to the shape of a side of a living body tissue having a different conductivity.

As understood by those skilled in the art, apparatuses of FIGS. 4 and 5 and the flow chart of FIG. 6 can be substantially applied even in case current distribution is determined by using impedance and voltage sources.

Embodiment 2

In this embodiment, an apparatus for measuring biocurrent distribution 40 is juxtaposed with the apparatus of the preceding embodiment and biocurrent distribution is determined more accurately by simultaneously considering biocurrent distribution within the head assumed from the surface potential and biocurrent distribution assumed from the surface magnetic field. Details of the apparatus for measuring biocurrent distribution are described in the aforementioned U.S. patent application Ser. No. 07/676077.

Figure 9:
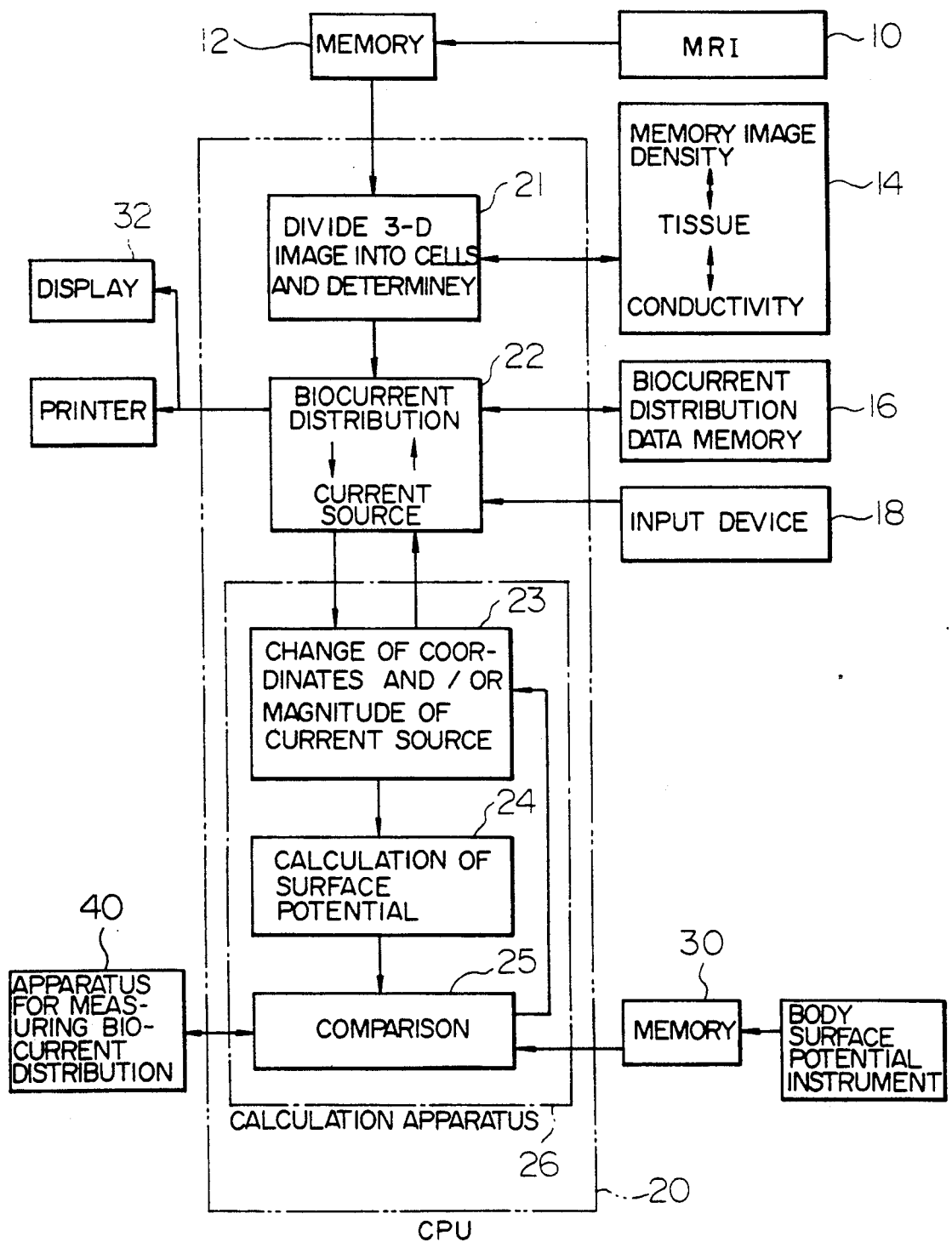
FIG. 9 is a block diagram showing the configuration of another embodiment of a biocurrent distribution determining apparatus according to the present invention.
Figure 10:
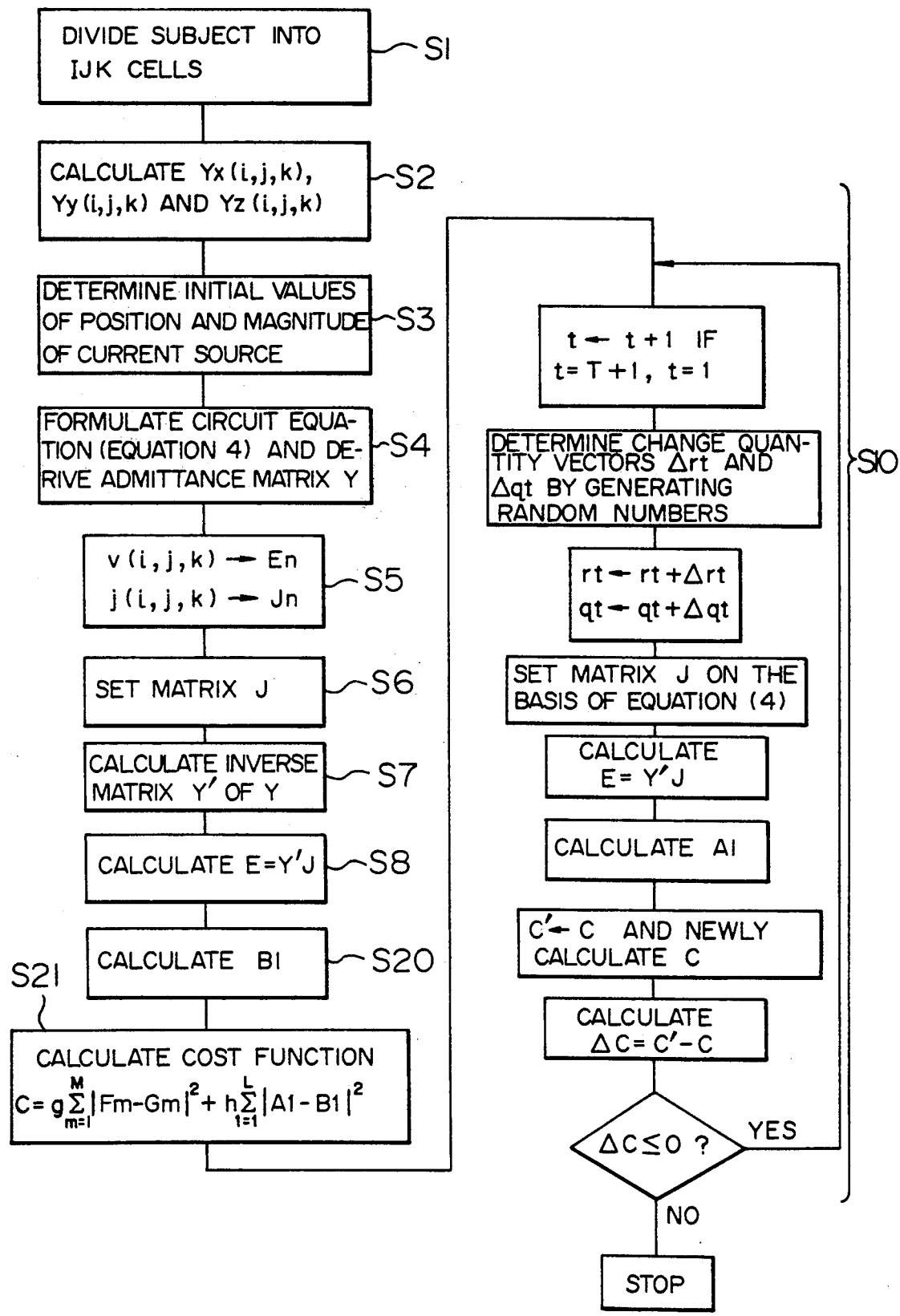
FIG. 10 is a flow chart for explaining the operation of the apparatus of FIG. 9.

FIG. 9 shows schematic configuration of this embodiment of a current distribution determining apparatus according to the present invention. FIG. 10 is the flow chart of its operation. The same devices and steps as those of the first embodiment are denoted by like characters and description of them will be omitted.

In order to measure the magnetic field on the surface of the head, sensors capable of measuring both potential and magnetic field are used as the sensors 42 of FIG. 4.

On the surface of the same subject, potential distribution Fm is measured by the living body surface potential measuring apparatus illustrated in FIG. 4 and magnetic field distribution A1 is measured by a magnetic field measuring apparatus. Therefore, the subject is replaced by the 3-dimensional network shown in FIG. 1, and the biocurrent distribution in the living body is estimated by using current sources as shown in FIG. 2. Potential Em at the same point as the point whereat potential has been measured on the living body surface is derived by means of equation (4), (8) or (11), and Gm is derived. Further, on the basis of assumed biocurrent distribution, magnetic field B1 obtained at the same point as the point whereat magnetic field has been measured on the living body surface is calculated by means of the following equation according to the Biot-Savart's law.

$$B1 = \frac{u}{4pi} \sum_{t=1}^{T} \frac{qtx(r1-rt)}{|r1-rt|^3} \quad (24)$$

Figure 11:
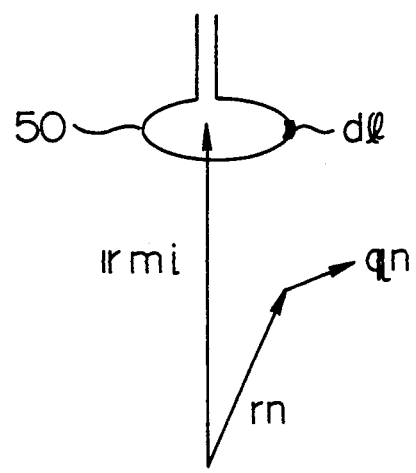
FIGS. 11 to 14 show coils for picking up magnetic fields.

In this equation, qt=(Jtx,Jty,Jtz), rn=(it,jt,kt), and r1 represents the position vectors of the measuring point. Alternatively, the shape of a pickup coil in the magnetic field measuring apparatus is considered. In case the pickup coil has no gradiometer as shown in FIG. 11, A1 is calculated by using the following equation.

$$A1 = \sum_{t=1}^{T} \int pt \cdot dl \quad (25)$$

In this equation, dl represents a line element located on a coil 50 and Pt represents a vector potential in the position of dl generated by a current dipole qt.

Figure 12:
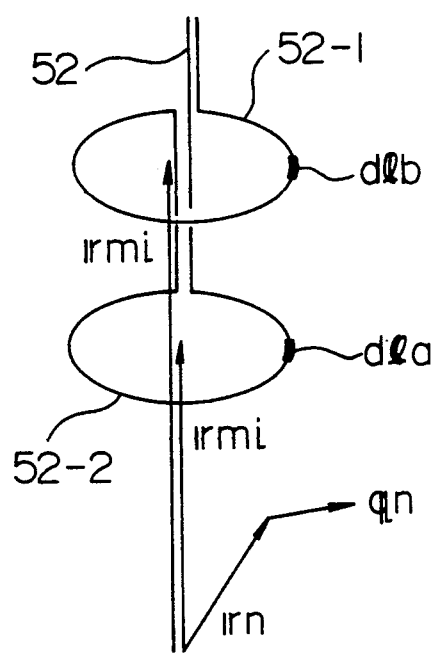
Figure 13:
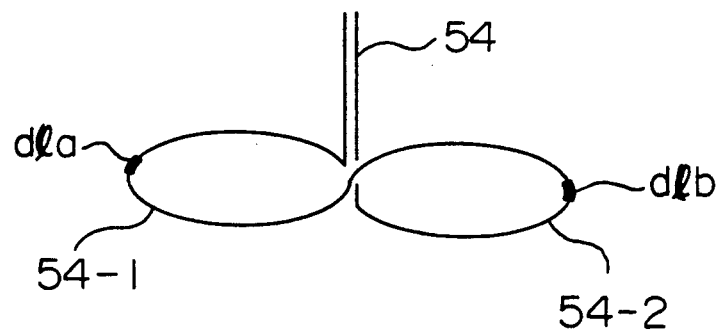

In case an axial-type or plane-type first-order differential coil is used as shown in FIGS. 12 and 13, A1 is calculated by using the following equation.

$$A1 = \sum_{t=1}^{T} \{\int pat \cdot d l a - \int pbt \cdot d l b\} \quad (26)$$

A pickup coil 52 includes a coil 52-1 and a coil 52-2, and d1a and d1b denote line elements on the coil 52-1 and 52-2, respectively. Pat and Pbt denote vector potentials in the positions of d1a and d1b generated by a current dipole qt. In FIG. 13, a pickup coil 54 includes a coil 54-1 and a coil 54-2.

Figure 14:
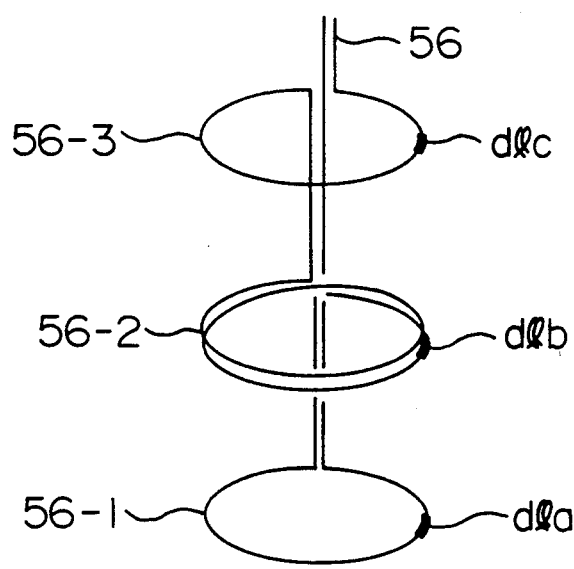

In case a second-order differential coil is used as shown in FIG. 14, A1 is calculated by using the following equation.

$$A1 = \sum_{t=1}^{T} \{\int pat \cdot d l a - 2\int pbt \cdot d l b - \int Pct \cdot d l c\} \quad (27)$$

A pickup coil 56 includes a coil 56-1, a coil 56-2, and a coil 56-3, and d1a, d1b and d1c denote line elements on the coil 56-1, the coil 56-2 and the coil 56-3, respectively. Pat, Pbt and Pct denote vector potentials in the positions d1a, d1b and d1c generated by a current dipole qt. We define the cost function by the following equation.

$$C = g \sum_{m=1}^{M} |Fm - Gm|^2 + h \sum_{l=1}^{L} |A1 - B1|^2 \quad (28)$$

Then qt=(Jtx,Jty,Jtz) and rt=(it,jt,kt) minimizing the cost function are selected (step 21). As constants g and h, such values that the position and magnitude of the current dipole can be empirically estimated in the best way are used. The solution thus selected is used as optimum estimated values of the position and magnitude of the current dipole.

In the equation 28, coefficients g and h are empirically determined, respectively.

Embodiment 3

Figure 15:
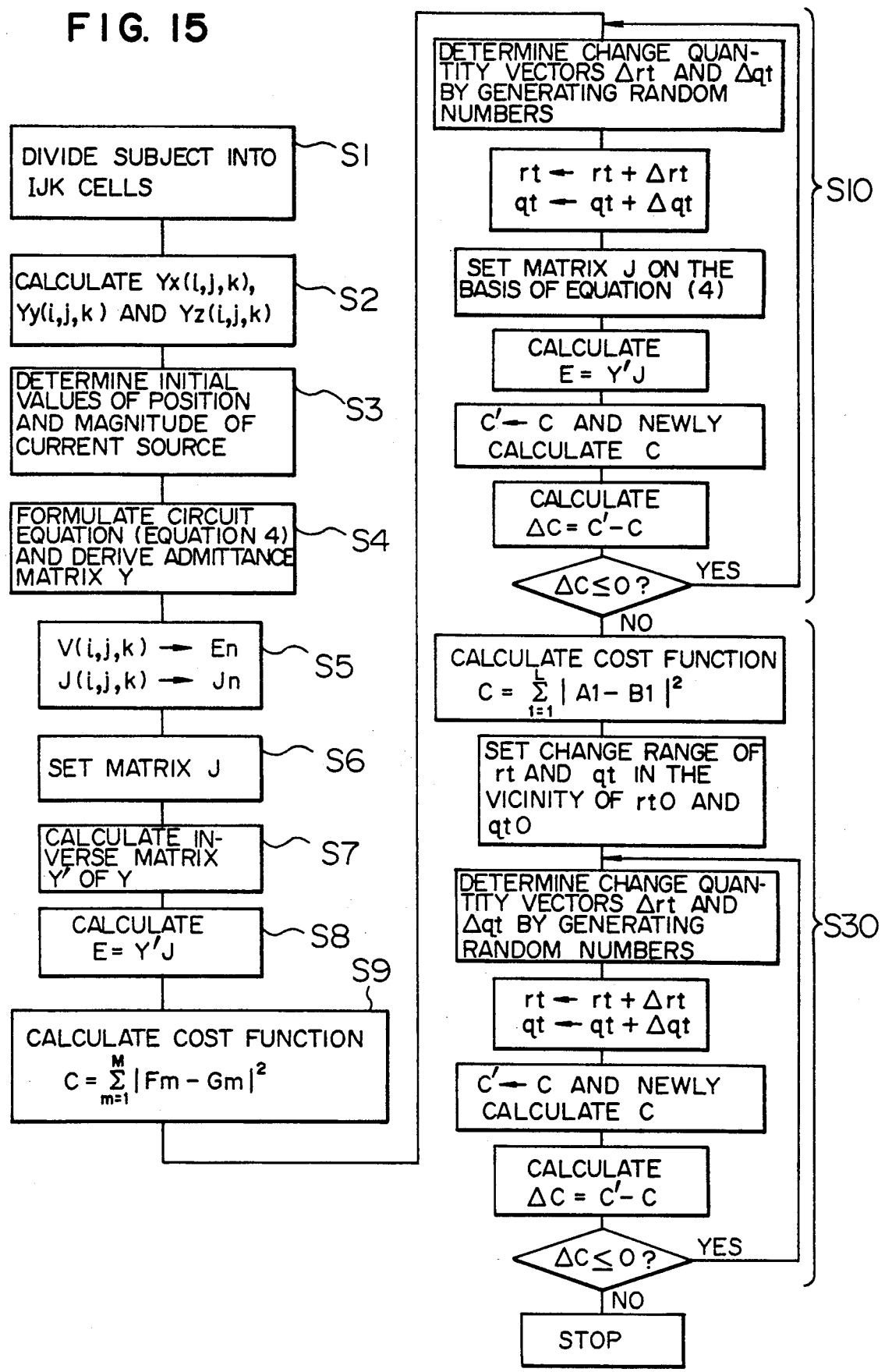
FIGS. 15 and 16 are flow charts showing other embodiments of a method for determining biocurrent distribution according to the present invention.

Another embodiment of the present invention will hereafter be described. The apparatus disclosed in FIG. 9 is used in this embodiment. Its operation is shown in FIG. 15. In FIG. 15, the same steps as those of FIG. 6 are provided with like characters.

In this embodiment, biocurrent distribution estimated by using the method of the embodiment 1 is corrected by using the apparatus for measuring biocurrent distribution. On the surface of the same subject, potential distribution Fm is measured by the living body surface potential measuring apparatus illustrated in FIG. 4 and magnetic field distribution A1 is measured by a magnetic field measuring apparatus. Therefore, the subject is replaced by the 3-dimensional network shown in FIG. 1, and the biocurrent distribution in the living body is estimated by using current sources as shown in FIG. 2. Potential Em at the same point as the point whereat potential has been measured on the living body surface is calculated according to the method of the embodiment 1, and Gm is derived. First of all, qt=(Jtx,Jty,Jtz) and rt=(it,jt,kt) minimizing the cost function expressed by the equation (9) are selected. Reliability of qt=(Jtx,Jty,Jtz) and rt=(it,jt,kt) thus derived as optimum estimated values depends upon the magnitude of a cell in the 3-D network used as the subject model and the signal-to-noise ratio of the measured data. When selecting qt=(Jtx,Jty,Jtz) and rt=(it,jt,kt) minimizing the cost function expressed by $$C = \sum_{l=1}^{L} |A1 - B1|^2 \quad (29)$$

by using the equation (24), (25), (26) or (27), it is assumed that the range of biocurrent distribution is confined in eight cells in the vicinity of qt=(Jtx,Jty,Jtz) and rt=(it,jt,kt) selected by minimizing the cost function expressed by the above described equation (9) such as the vicinity of the node (it,jt,kt) (step 30).

As for the method for finding the minimum value of the cost function expressed by the equation (9) or (29), the steepest descent method (as described in "Mathematical Programming Practice" written by Eitaro Aiyoshi and Kiyotaka Shimizu and published by Asakura Shoten), Newton method, or simulated annealing method (as described in SPIE, Vol. 1351, pp.410-416, 1990) can be mentioned.

Figure 16:
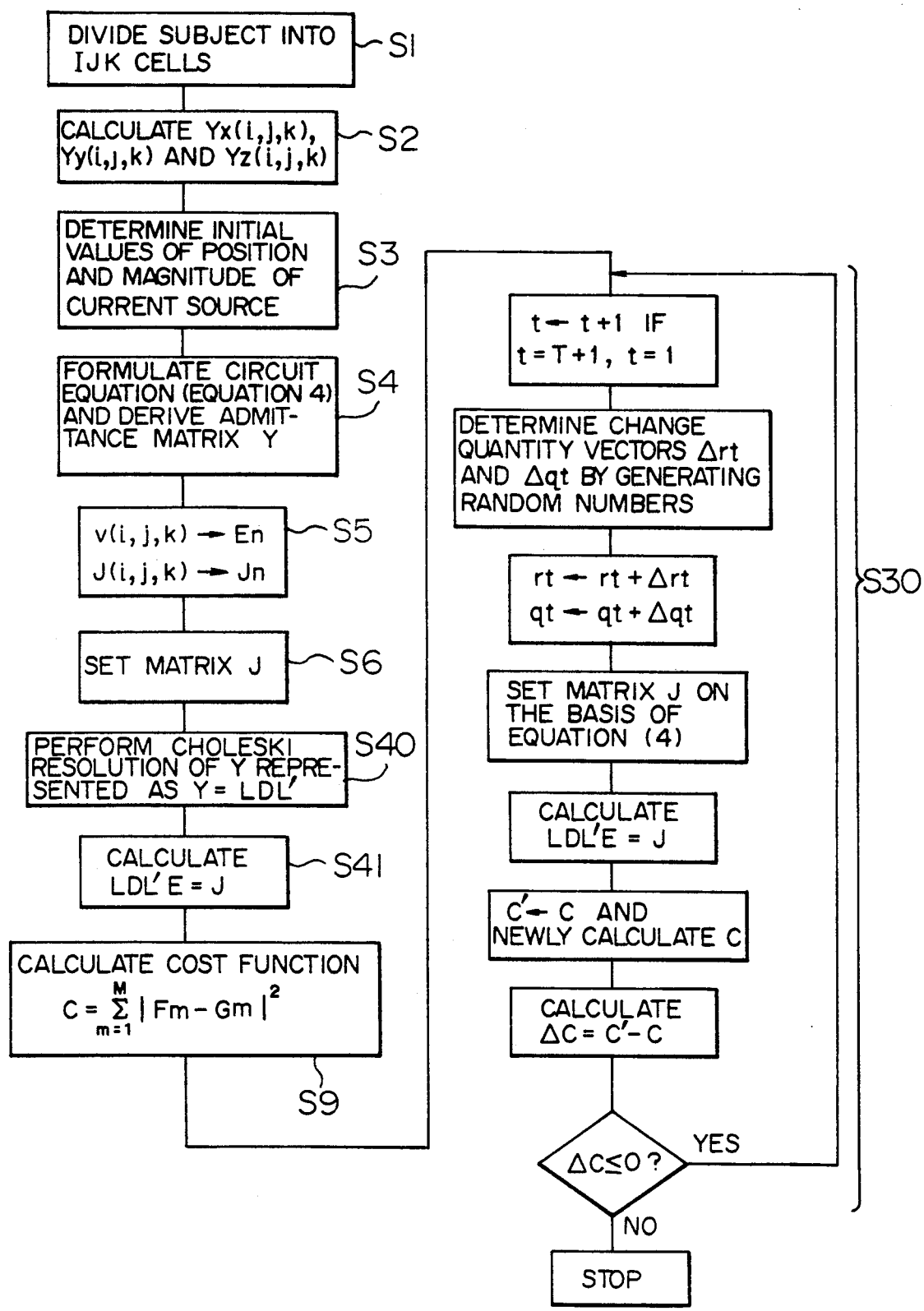

In general, the matrix Y becomes a large matrix having several tens thousand elements. When the potential V(i,j,k) at a node is to be derived, therefore, the simultaneous equations (7) may be directly solved instead of deriving the inverse matrix Y'. In this case, however, potential at every node must be calculated. As for the technique for solving the simultaneous equations, the Gauss method, modified Choleski method, and SOR method (as described in "Numerical Calculation of Matrix pp. 56-61" written by Hayato Togawa and published by OHM SHA LTD.) can be mentioned. FIG. 16 shows a flow chart of the case where the simultaneous equations are solved by using the modified Choleski method to assume the positions and magnitudes of current dipoles. In steps 40 and 41 of FIG. 16, L is a lower triangular matrix having diagonal elements of 1 and D is a diagonal matrix. L' is a transposed matrix. Further, in FIG. 16, the same steps as those of FIG. 6 are denoted by like numerals and will not be described.

Japanese patent application No. Hei-3-202720 is hereby incorporated herein by reference.

Owing to the present invention, positions and magnitudes of current dipoles within a living body can be estimated from potential distribution data on the surface of the living body which can be measured comparatively easily. Further, when potential distribution on the surface of the living body is to be calculated from assumed current dipoles, it becomes possible to take the shape of the living body and conductivity distribution within the living body into consideration. As a result, it is possible to assume positions and magnitudes of current dipoles generating potential distribution on the surface of the living body which coincides with measured data with high precision.

Although the present invention has been described in detail, it should be understood that various changes, substitutions and alterations can be made hereto without departing from the spirit and scope of the present invention as defined by the appended claims.

We claim:

1. A method for determining biocurrent distribution within a subject, comprising the steps of:
   measuring potentials at a plurality of points on a surface of said subject;
   deriving physical properties of said subject in positions of a 3-D network of predetermined cells in said subject;

determining admittances of lines defining external shapes of said cells on the basis of said physical properties;

calculating potentials of nodes of positions corresponding to at least said measuring points in a 3-D network formed by said lines, on the basis of the admittances of said lines and biocurrent distribution within said subject and wherein at least one current source is connected in parallel with said lines;

changing position and current magnitude of each of said at least one current source while comparing said calculated potentials with said measured potentials, and determining the positions and current magnitudes of the at least one current source on the basis of said comparing and determining said biocurrent distribution from said positions and current magnitudes of the at least one current source.

2. A method according to claim 1, wherein said physical properties are conductivity.

3. A method according to claim 2, wherein said step of deriving conductivities of cells comprises the steps of:

dividing a 3-D magnetic resonance image or X-ray image of said subject into pixels respectively corresponding to said cells; and deriving conductivities of said pixels.

4. A method according to claim 3, wherein said pixel conductivities are discriminated on the basis of proportion, in said cell, of a living body tissue which can be discriminated by said magnetic resonance or X-ray and which has a known conductivity.

5. A method according to claim 3, wherein said pixel conductivities comprise a value obtained by multiplying conductivity of a living body tissue in each pixel by the proportion of said living body tissue in said pixel and summing the resultant products.

6. A method according to claim 1, wherein said current source determining step comprises the step of determining said at least one current source so as to minimize total source current over all of said measuring points, of integer-th power of absolute value of difference between said calculated potential and said measured potential.

7. A method according to claim 1, wherein said potential calculating step comprises the step of formulating simultaneous equations based on Kirchhoff's first law with respect to all nodes of the above described 3-D network and solving the simultaneous equations.

8. A method according to claim 7, wherein said cells comprise cubes and said 3-D network formed by the lines comprises said 3-D cubic cell network, and said step of calculating potentials of nodes in said 3-D network comprises the steps of:

making an element of an mth row of an nth column in a coefficient matrix equivalent to the sum of admittances of lines connected to an mth node when m is equivalent to n;

making an element of an mth row of an nth column in said coefficient matrix equivalent to the product of the admittance of a line located between the mth node and an adjacent nth node and −1 when m is different from n; and making a column vector having potential at the mth node as an element equivalent to product of a column vector having a sum of at least one currents flowing from current source connected to said node as an element and an inverse matrix of said coefficient matrix.

9. A method according to claim 8, wherein said step of calculating potentials of nodes in said 3-D network comprises the steps of:

making potential at an mth node equivalent to the product of a column vector having sum of currents flowing from at least one current source connected to said node as an element and a row vector having an mth row of an inverse matrix of said coefficient matrix as an element; and calculating potentials of at least one node simultaneously in a parallel processing computer.

10. A method according to claim 1, wherein predetermined nodes of said 3-D network coincide with points located on the surface of said subject where a voltage has been measured.

11. A method according to claim 1, wherein said cells are shape of a triangular pyramid.

12. A method according to claim 1, wherein cells in said subject each contact an interface of a portion having a different conductivity are the shape of triangular pyramid whereas other cells are the shape of rectangular parallelepiped.

13. A method according to claim 1, further comprising the steps of:

measuring magnetic fields at a plurality of second points on the surface of said subject;

calculating magnetic fields at said second points on the basis of said determined biocurrent distribution; and changing the positions and/or magnitudes of said determined at least one current source while comparing said calculated magnetic fields with said measured magnetic fields, and correcting said biocurrent distribution on the basis of said comparing.

14. A method according to claim 13, wherein said biocurrent distribution correcting step comprises the step of correcting the position and magnitude of each of said at least one current source so that the sum total of integer-th powers of absolute values of differences between said calculated magnetic fields and said measured magnetic fields for all of said second points is minimized.

15. A method according to claim 13, wherein said second points coincide with said points where a potential has been measured.

16. A method for determining biocurrent distribution within a subject, comprising the steps of:

measuring potentials at a plurality of points on a surface of said subject;

measuring magnetic fields at said points;

deriving physical properties of said subject in positions of a 3-D network of predetermined cells in said subject;

determining admittances of lines defining external shapes of said cells on the basis of said physical property;

calculating potentials of nodes of positions corresponding to at least said measuring points in a 3-D network formed by said lines, on the basis of the admittances of said lines and biocurrent distribution within said subject and wherein at least one current source is connected in parallel with said lines;

calculating magnetic fields at said measuring points on the basis of said biocurrent distribution; and determining current vectors and positions thereof and minimizing the sum of the product obtained by multiplying a sum total of integer-th power values of absolute values of differences between said calculated potentials and said measured potentials for all of said measuring points by a first predetermined coefficient and the product obtained by multiplying the sum total of integer-th power values of absolute values of differences between said calculated magnetic fields and said measured magnetic fields for all of said measuring points by a second predetermined coefficient.

17. A method for determining biocurrent distribution within a subject, comprising the steps of:
   measuring potentials at a plurality of points on a surface of said subject;
   deriving physical properties of said subject in positions of a 3-D network of predetermined cells in said subject;
   determining impedances of lines defining external shapes of said cells on the basis of said physical properties;
   calculating potentials of nodes of positions corresponding to at least said measuring points in a 3-D network formed by said lines, on the basis of the impedances of said lines biocurrent distribution within said subject and wherein at least one current source is connected in parallel with said lines;
   changing position and voltage magnitude of each of said at least one voltage source while comparing said calculated potentials with said measured potentials, and determining the positions and voltage magnitudes of the at least one voltage source on the basis of said comparing; and
   determining said biocurrent distribution from said positions and current magnitudes of the at least one voltage source and said impedances.

18. A method according to claim 17, wherein said potential calculating step comprises the steps of:
   formulating simultaneous equations for all lines of said 3-D network according to Kirchhoff's second law;
   calculating currents flowing through all lines by solving said simultaneous equations;
   deriving potential difference across each line on the basis of a current flowing through each line and impedance of that line; and
   calculating potentials at said measuring points on the basis of said potential difference.

19. An apparatus for determining biocurrent distribution within a subject, comprising:
   means for measuring potentials at a plurality of points on a surface of said subject;
   means for deriving physical properties of said subject in positions of predetermined cells in said subject, said cells forming a 3-D arrangement;
   means for determining admittances of lines defining an external shape of each of said cells on the basis of said physical properties;
   means for setting at least one current source connected in parallel with said lines on the basis of biocurrent distribution in said subject;
   means for calculating potentials of nodes of positions corresponding to at least said measuring points in a 3-D network formed by said lines, on the basis of the admittances of said lines and said current sources connected in parallel with said lines;
   means for changing positions and current magnitudes of said at least one current source while comparing said calculated potentials with said measured potentials, and determining the positions and current magnitudes of the at least one current source on the basis of said comparing; and
   means for determining said biocurrent distribution from said positions and current magnitudes of the at least one current source.

20. An apparatus according to claim 19, further comprising:
   means for measuring magnetic fields at a plurality of second points on the surface of said subject;
   means for calculating magnetic fields at said second points on the basis of said determined biocurrent distribution; and
   means for changing, the positions and/or magnitudes of said determined at least one current source while comparing said calculated magnetic fields with said measured magnetic fields, and correcting the positions and magnitudes of said at least one current source on the basis of said comparing.

21. An apparatus for determining biocurrent distribution within a subject, comprising:
   means for measuring potentials at a plurality of points on a surface of said subject;
   means for measuring magnetic fields at said points;
   means for deriving physical properties of said subject in positions of predetermined cells in said subject, said cells forming a 3-D arrangement;
   means for determining admittances of lines defining an external shape of each of said cells on the basis of said physical properties;
   means for setting at least one current source connected in parallel with said lines on the basis of biocurrent distribution in said subject;
   means for calculating potentials of nodes of positions corresponding to at least said measuring points in a 3-D network formed by said lines, on the basis of the admittances of said lines and said at least one current source connected in parallel with said lines;
   means for calculating magnetic fields at said measuring points on the basis of said biocurrent distribution; and
   means for determining positions and magnitudes of said at least one current source and minimizing the sum of the product obtained by multiplying a sum total of integer-th power values of absolute values of differences between said calculated potentials and said measured potentials for all of said measuring points by a first predetermined coefficient and the product obtained by multiplying the sum total of integer-th power values of absolute values of differences between said calculated magnetic fields and said measured magnetic fields for all of said measuring points by a second predetermined coefficient.

22. An apparatus for determining biocurrent distribution within a subject, comprising:
   means for measuring potentials at a plurality of points on a surface of said subject;
   means for deriving physical properties of said subject in positions of predetermined cells in said subject, said cells forming a 3-D arrangement;
   means for determining impedances of lines defining an external shape of each of said cells on the basis of said physical properties;

means for setting at least one voltage source connected in series to said lines on the basis of biocurrent distribution in said subject;

means for calculating potentials of nodes of positions corresponding to at least said measuring points in a 3-D network formed by said lines, on the basis of the impedances of said lines and said voltage sources connected in series to said lines;

means for changing positions and voltage magnitudes of said at least one voltage source while comparing said calculated potentials with said measured potentials, and determining the positions and voltage magnitudes of the at least one voltage source on the basis of a result of comparison; and means for determining said biocurrent distribution on the basis of determined voltage sources and said impedances.

* * * * *